United States Patent
Kurosaka et al.

(10) Patent No.: US 7,994,478 B2
(45) Date of Patent: Aug. 9, 2011

(54) INSPECTION APPARATUS USING ELECTROMAGNETIC WAVES

(75) Inventors: Ryoji Kurosaka, Kawasaki (JP); Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 1021 days.

(21) Appl. No.: 11/843,423

(22) Filed: Aug. 22, 2007

(65) Prior Publication Data

US 2008/0048678 A1 Feb. 28, 2008

(30) Foreign Application Priority Data

Aug. 28, 2006 (JP) ................................. 2006-230159
Mar. 13, 2007 (JP) ................................. 2007-063673

(51) Int. Cl.
*G01J 5/02* (2006.01)
*G01R 27/00* (2006.01)
*G01R 27/22* (2006.01)

(52) U.S. Cl. ................. 250/341.1; 250/343; 250/458.1; 324/637; 356/316

(58) Field of Classification Search .............. 250/458.1, 250/340, 341.1, 343; 356/316; 324/637, 324/612

See application file for complete search history.

(56) References Cited

U.S. PATENT DOCUMENTS

| | | | |
|---|---|---|---|
| 2003/0040004 A1* | 2/2003 | Hefti et al. ................. 435/6 |
| 2007/0148047 A1 | 6/2007 | Itsuji | |
| 2007/0215810 A1 | 9/2007 | Kurosaka et al. .......... 250/358.1 |
| 2007/0252992 A1 | 11/2007 | Itsuji ........................... 356/369 |
| 2007/0279136 A1 | 12/2007 | Koyama et al. ............ 331/107 T |
| 2007/0279143 A1 | 12/2007 | Itsuji ........................... 331/185 |
| 2008/0116374 A1 | 5/2008 | Ouchi et al. ................. 250/306 |

FOREIGN PATENT DOCUMENTS

JP 2006-153852 A 6/2006

OTHER PUBLICATIONS

T. Ohkubo, et al., "Micro-strip-line-based sensing chips for characterization of polar liquids in terahertz regime", Applied Physics Letters 88, 212511, 2006.

* cited by examiner

*Primary Examiner* — David Porta
*Assistant Examiner* — Jessica L Eley
(74) *Attorney, Agent, or Firm* — Fitzpatrick, Cella, Harper & Scinto (57) ABSTRACT

An inspection apparatus for acquiring information on a measurement object using electromagnetic waves, comprising a substrate; a transmission line that is formed on the substrate; an electromagnetic wave generating unit for supplying an electromagnetic wave to the transmission line; an electromagnetic wave detecting unit for detecting the electromagnetic wave that has propagated through the transmission line; and a walled structure. The walled structure includes a side wall portion that extends along the transmission line within a region in which the electromagnetic wave that propagates through the transmission line and the measurement object interact with each other.

13 Claims, 11 Drawing Sheets

INSPECTION APPARATUS USING ELECTROMAGNETIC WAVES

BACKGROUND OF THE INVENTION

1. Field of the Invention

The present invention relates to an inspection apparatus and an inspection method for acquiring information (physical properties, identification, concentration, presence, etc.) on a detection object using electromagnetic waves. In particular, the present invention relates to an inspection apparatus and an inspection method using electromagnetic waves of frequencies including at least a part of a frequency range of from 30 GHz to 30 THz (called "terahertz waves" in the present specification).

2. Description of the Related Art

In recent years, attention has been paid to a technique using terahertz waves with the development of a unit for generating and detecting the terahertz waves. For example, as an applied field of terahertz waves, there is a technique that conducts imaging using terahertz waves as a safe fluoroscopic inspection apparatus to replace X-rays. Also, researches and developments are made on a spectroscopic technique for inspecting an absorption spectrum or complex dielectric constant of a material to check a bonding state, a technique for analyzing a biologic molecule, and a communication technique.

Figure 16A:
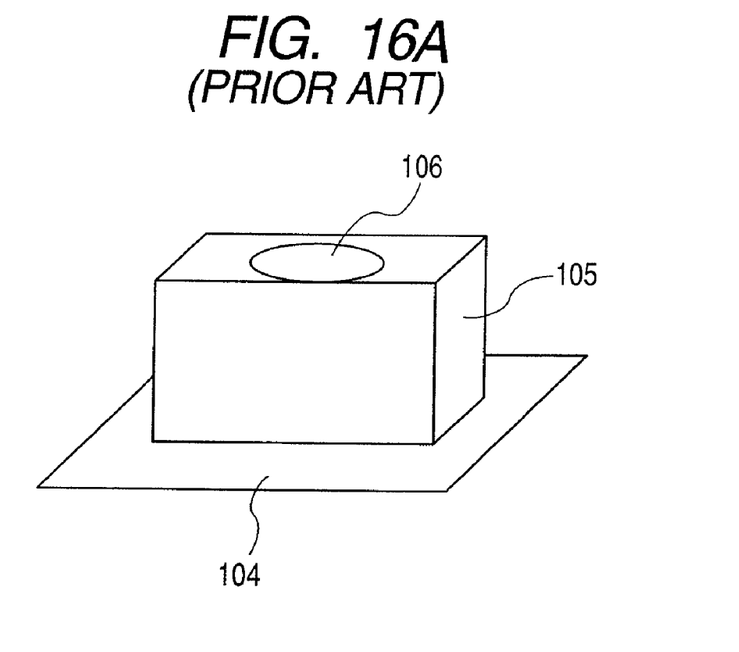
FIGS. 16A and 16B are diagrams illustrating an inspection apparatus in the prior art.
Figure 16B:
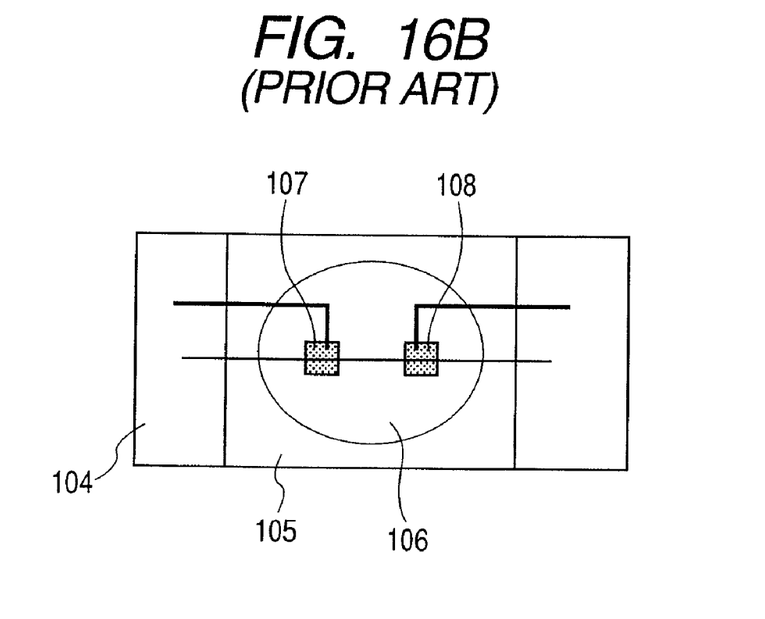

Appl. Phys. Lett., 88, 212511, 2006 discloses an article related to a transmission line terahertz sensor in association with the above-mentioned technique. Reference numerals 104 to 108 in FIGS. 16A and 16B schematically illustrate a transmission line terahertz sensor of Appl. Phys. Lett., 88, 212511, 2006. In this example, a terahertz wave generation section 107 and a terahertz wave detection section 108 are integrated together on a substrate 104, a polyethylene vessel 105 is located so as to include those members therein, and a detection object is introduced from a detection object introduction hole 106.

Also, there is disclosed a technique in which a detection object is arranged in the vicinity of a transmission line with a periodicity of a certain wavelength order in a transmission line terahertz sensor (refer to Japanese Patent Application Laid-Open No. 2006-153852). In both techniques, the detection object is deposited on or in the vicinity of a transmission line. Then, electromagnetic waves that are propagated in a transmission line and the detection object interact with each other, to thereby operate as the transmission line terahertz sensor.

SUMMARY OF THE INVENTION

As a method of applying a detection object, there is proposed a method in which a solution containing the detection object in a solvent (for example, phosphate buffer solutions for DNA) is prepared, and the solution is applied on a transmission line using a small amount dropping device such as a micro injector. It has been found that the controlled dropping amount of the drop device can be controlled on the several tens of picoliters order in a case where the density of a solution is sufficiently low, but the controllable amount of a solution is increased as the density becomes higher. When the density of a solution is sufficiently low, a micro droplet of the several tens of picoliters order can be dropped, so a region where the dropped solution is present can be controlled only to the vicinity of the transmission line. However, when the density of solution is high, and the controllable amount of droplet (for example, several tens of nanoliters order) is increased, it has been confirmed that the region exceeds the transmission line and widely spreads. After the solution that has dropped on the transmission line has dried, the detection object is present with a certain distribution in the region where the solution used to be present. More specifically, the detection object is selectively formed in a toric configuration or a ring configuration on the outer side of the region where the solution used to be present depending on the material or flatness of a substrate that is a base. Hereinafter, a portion that is formed in the toric confirmation or the ring configuration is also referred to as a "meniscus portion".

The above-mentioned phenomenon can be described as follows in terms of the influence of a convection flow that is caused by a difference in solute density which is induced by evaporation or gravity force of the solution. A detection object that has uniformly dissolved in a solution is formed on the substrate in a substantially hemispherical configuration after the solution has dropped using a micro injector. The solution formed in the substantially hemispherical configuration is evaporated from a surface of the solution which is in contact with a gas phase or the atmosphere, with the result that the solute density becomes higher on the outer side of the substantially spherical configuration than the inner side thereof. Accordingly, the density gradient of the solute density occurs, and then there occurs such a density convection that a portion which is higher in the density of the detection object (that is, outside of the solution) goes around and gets under a portion that is lower in the density of the detection object (that is, inner side of the solution). In this case, the evaporation of the solution is advanced and thus the detection object is deposited in the meniscus configuration.

Figure 14:
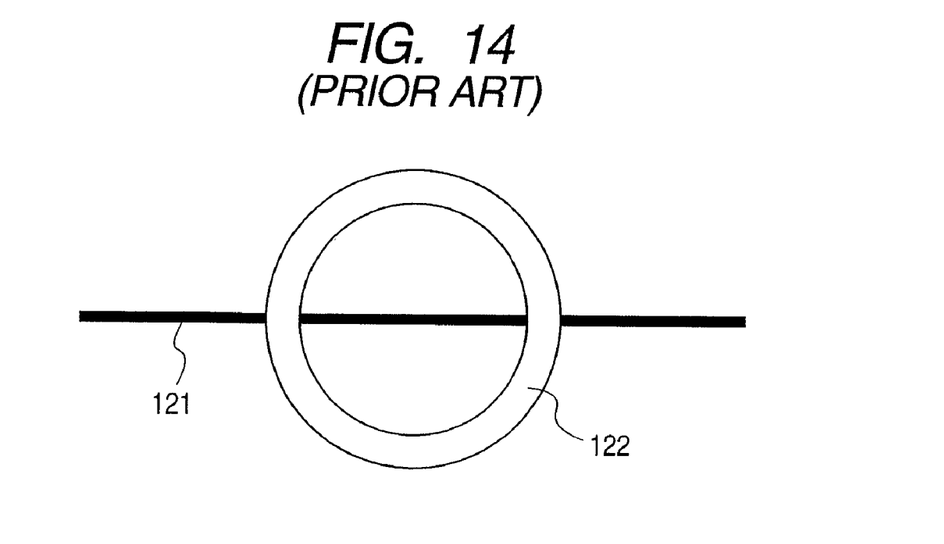
FIG. 14 is a plan view illustrating a detection object that is formed on a transmission line in the prior art.

As described above, in a case where the controllable amount of dropped solution is large, as illustrated in FIG. 14, the detection object is formed on a transmission line 121 in a toric configuration 122 in a wide region including the transmission line 121. In this case, it is estimated that a part of the detection object, more specifically, only the detection object that is present in a region close to a portion where the transmission line 121 and the toric configuration 122 overlap with respect to the amount of dropped detection object contributes to the interaction with electromagnetic waves that propagate through the transmission line.

Under the circumstances, in order to increase a region of the interaction with the electromagnetic wave that propagates in the transmission line, there is an approach in which the region where the solution is distributed is limited, and the detection object is deposited so as to fill the inside of the meniscus portion. In this case, when the density of the solution is high, the solution does not enter the region, depending on how the region is sectioned. As a result, it is desirable to set an appropriate region according to the density of the solution. In this case, in order to fill the region with a sample to be measured, a considerable amount of solution may be required. The region in which the interaction between the electromagnetic waves that propagate through the transmission line and the detection object is conducted is in the vicinity of the transmission line. For that reason, it is estimated that the region of the transmission line that contributes to the sensing is large, but the amount of the detection object that contributes to the operation of the sensor is small compared to the detection object used.

As described above, in the transmission line terahertz sensor, there is room for improvement in the use efficiency of the detection object.

In view of the above-mentioned problems, an object of the present invention is to provide an inspection apparatus for acquiring information on a measurement object using electromagnetic waves. The inspection apparatus presents the following features.

An inspection apparatus according to the present invention is an inspection apparatus for acquiring information on a measurement object using electromagnetic waves, including: a substrate; a transmission line that is formed on the substrate; an electromagnetic wave generating unit for supplying an electromagnetic wave to the transmission line; an electromagnetic wave detecting unit for detecting the electromagnetic wave that has propagated through the transmission line; and a walled structure, in which the walled structure includes a side wall portion that extends along the transmission line within a region in which the electromagnetic wave that propagates through the transmission line and the measurement object interact with each other.

Also, the inspection apparatus according to the present invention includes a transmission line formed on a substrate for propagating electromagnetic waves, an electromagnetic wave generating unit for generating and supplying an electromagnetic wave to the transmission line, an electromagnetic wave detecting unit for detecting the electromagnetic wave that has propagated through the transmission line, and a walled structure. The walled structure includes a side wall portion that extends along the transmission line within a region where a measurement object interacts with the electromagnetic wave that propagates through the transmission line and rises from a surface of the substrate toward the inside of the region.

Further, in view of the above-mentioned problems, according to the present invention, there is provided an inspection method for acquiring information on a measurement object using the inspection apparatus, the inspection method including detecting results of the interaction between a detection object within a measurement object and an electromagnetic wave that propagates through the transmission line to inspect the detection object. Still further, according to the present invention, there is provided an inspection method for acquiring information on a measurement object using the inspection apparatus having a temperature-dependence monitoring unit for monitoring the temperature dependence of a detection object within the measurement object which is dropped on the substrate. The inspection method includes detecting temperature dependence of the interaction between the detection object within the measurement object and the electromagnetic wave that propagates through the transmission line to inspect the detection object.

In the inspection apparatus and method according to the present invention, a measurement object is analyzed or its information is acquired using an electromagnetic wave containing a frequency component in a frequency region of typically 30 GHz or higher and 30 THz or lower. Further, in order to acquire a fingerprint spectrum of a biomaterial, etc., it is desirable to use an electromagnetic wave containing a frequency component of a range of about 0.1 THz to 10 THz.

According to the inspection apparatus and method of the present invention, it is possible to effectively make use of the detection object by providing the walled structure.

Further features of the present invention will become apparent from the following description of exemplary embodiments with reference to the attached drawings.

DESCRIPTION OF THE EMBODIMENTS

Hereinafter, a description will be given of embodiments of an inspection apparatus and method according to the present invention. In the embodiments, there is provided a walled structure that assists a meniscus portion of a detection object which is precipitated from a measurement object such as a solution so as to be deposited on or in the vicinity of a transmission line or assists a detection object within a measurement object such as a solution so as to remain in such region, so that the detection object spreads over a region where the transmission line is formed.

It is desirable that the walled structure include a side wall portion that extends along the transmission line in a region where an electromagnetic wave that propagates through the transmission line and the measurement object interact with each other.

For example, in a region where an electric field distribution of an electromagnetic wave that propagates through the transmission line extends to cause interaction with the electromagnetic wave, there is provided a walled structure having a portion that rises from a surface on which the transmission line is formed toward the inside of that region to form a side wall portion. The range of that region is defined, for example, as a portion including a region in which there exists an electric field of $1/e^2$ or more of a peak value of the electric field distribution of the propagation electromagnetic wave. When the walled structure is located at the above-mentioned portion, the deposited detection object and the electromagnetic wave efficiently interact with each other, thereby enabling the propagation state of the electromagnetic wave that propagates through the transmission line to be effectively influenced.

One configuration of the walled structure is the above-mentioned deposition assist structure that helps at least a part of a detection object that is precipitated from a measurement object which is dropped on a substrate to deposit within the region where the detection object interacts with the electromagnetic wave that propagates through the transmission line. However, the walled structure can also function as a restraint assist structure for helping at least a part of the detection object within the measurement object which is dropped on the substrate to be restrained to the region in which the detection object interacts with the electromagnetic wave that propagates through the transmission line. A typical example of the walled structure having a role of helping the detection object within the measurement object such as a solution to remain in the region on or in the vicinity of the transmission line is found in a case in which the measurement object is frozen and retained as in a fourth embodiment that will be described later. In this case, before the detection object is precipitated from the measurement object such as the solution to form a meniscus portion, the measurement object that is restrained within the region is frozen and subjected to measurement. The following description is mainly given of a deposition assist structure that assists the meniscus portion in being selectively deposited on or in the vicinity of the transmission line. The deposition assist structure can be employed as a restraint assist structure that assists the detection object within the measurement object in being restrained within such region.

Figure 3:
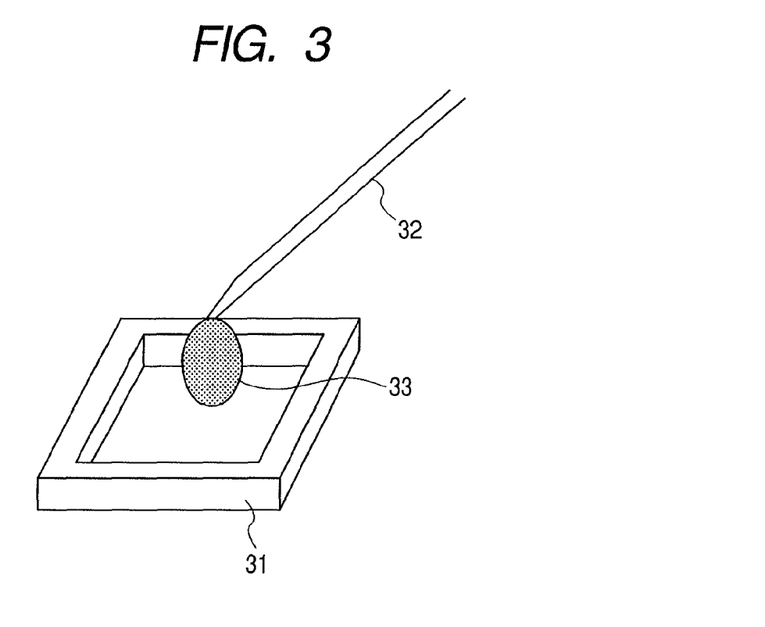
FIG. 3 is a perspective view schematically illustrating the example of the liquid holding structure.

As the deposition assist structure for helping the meniscus portion of the detection object that is precipitated from the measurement object such as the solution to be deposited on or in the vicinity of the transmission line, there is, for example, a dam-shaped liquid holding structure illustrated in FIG. 3. For example, when a solution 33 containing the detection object is dropped in the interior of a liquid holding structure 31 from a micro injector 32, the solution is reserved in the interior of the liquid holding structure 31, and the detection object is deposited while being affected by the configuration and material of the inner wall of the liquid holding structure 31. The side wall portion of the inside of the liquid holding structure 31 is formed on a side which is in the vicinity of the transmission line and in a direction of spreading the solution (typically, the side wall portion is configured so as to surround the region having the transmission line). As a result, it is possible to selectively deposit the detection object on or in the vicinity of the transmission line. As described above, the above-mentioned structure can be used as a restraint assist structure that plays a role of assisting the detection object within the solution in being restrained within the region on or in the vicinity of the transmission line.

Figure 4:
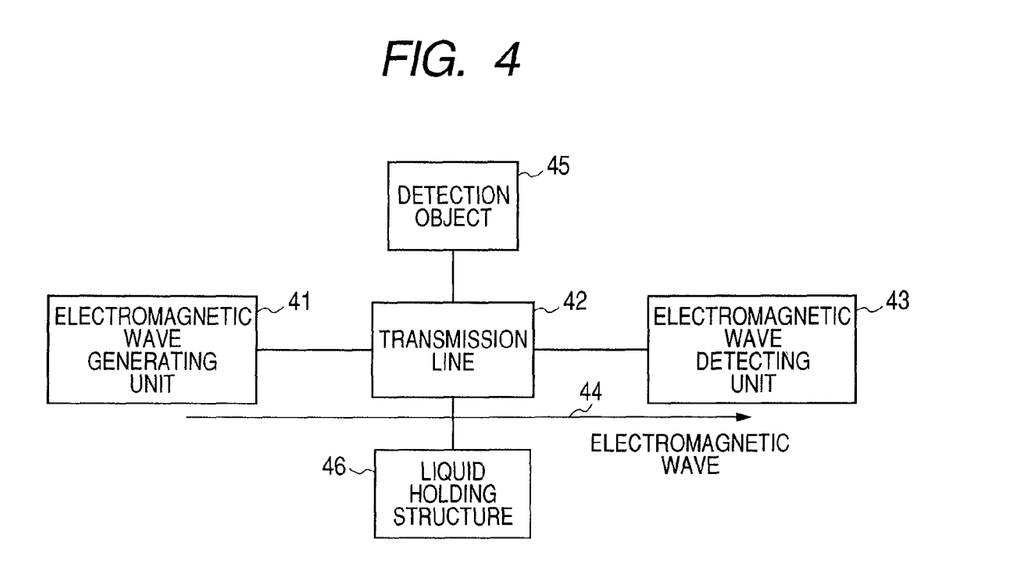
FIG. 4 is a block diagram illustrating a conceptual structure according to an embodiment of the present invention.

Now, a conceptual structural example used in applying the present invention will be described with reference to FIG. 4. FIG. 4 illustrates: an electromagnetic wave generating unit 41 that generates terahertz waves; a transmission line 42 that transmits the terahertz waves; and an electromagnetic wave detecting unit 43 that detects the terahertz waves. Also, FIG. 4 illustrates: an electromagnetic wave 44 including at least a part of frequency bands having frequencies of 30 GHz to 30 THz; a detection object 45 within a measurement object; and a liquid holding structure 46 for helping a meniscus portion of the detection object which is precipitated from the measurement object such as the solution to be selectively deposited on the transmission line 42. In the liquid holding structure 46 of the present invention, a region of at least a part of the structures for assisting the detection object 45 in being selectively deposited on or in the vicinity of the transmission line 42 exists along the transmission line 42 in the vicinity of the transmission line. Further, the structure has a higher-level surface than the surface on which the detection object 45 is dropped which forms a step so that the measurement object including the detection object 45 is confined to a certain region by the side wall portion which is formed by the step portion (refer to FIG. 3).

The frequency range of the terahertz waves (30 GHz to 30 THz) is such a frequency range that there appears a characteristic change which is attributable to the interaction between molecules or change in stereochemical structure of molecules. For that reason, this range is suitable in observing a macroscopic change in the characteristics of molecules.

As the electromagnetic generating unit 41 that generates terahertz waves and supplies the terahertz to the transmission line 42, there is a method of integrating photoconductive elements using a low-temperature grown gallium arsenide (LT-GaAs). Also, there is a method of inputting the terahertz waves to a device using an external connection unit such as a parametric generator, a backward-wave oscillator (BWO), a quantum cascade laser, or an antenna. Further, as the electromagnetic detecting unit 43 for detecting the terahertz waves, there is used a photoconductive element using LT-GaAs. However, the present invention is not limited thereto, but can use an electro-optic crystal (EO crystal), a bolometer, a superconductive tunnel junction device, or Schottky diode.

The detection object 45 is, for example, dissolved in a solvent, and the resulting solution is applied on the transmission line using a small quantity coating unit such as a micro injector (not shown). For example, when DNA is to be analyzed as the detection object 45, DNA is immersed in a phosphate buffer solution. For example, the DNA density is 0.5 μg/μl, and the amount is several tens of nl. The liquid holding structure 46 restrains a region where the detection object 45 is present after the solution has been dropped, and in this example, the liquid holding structure 45 is a tub structure that is made of dielectric material and is several μm in height. The liquid holding structure 46 enables the solution to be confined to the structure with the result that the arrangement position control of the detection object 45 can be readily conducted.

In the case where the base of the liquid holding structure 46 (a place on which the solution is dropped) is flat, the detection object 45 is deposited in a meniscus fashion along the outer periphery of the configuration (that is, a configuration extending along the line of intersection between the side wall of the liquid holding structure 46 and the base) when the solution is dropped and retained on the substrate. Because the base that has been subjected to processing such as plasma etching has unevenness, the detection object that has been restrained and retained by the liquid holding structure 46 is deposited not in the meniscus configuration but in the configuration corresponding to the uneven pattern of the base. This configuration is not so desirable, but in any cases, it is possible to deposit the detection object into the meniscus configuration or the configuration corresponding to the uneven pattern, on or in the vicinity of the transmission line. As a result, it is possible to increase the interaction region between the electromagnetic wave 44 that propagates through the transmission line 42 and the detection object 45.

As described above, in the inspection apparatus according to the above embodiment, with the provision of the deposition assist structure, it is possible to increase the interaction region between the electromagnetic wave 44 that propagates through the transmission line 42 and the detection object 45. Also, it is possible to enhance the use efficiency of the detection object.

Next, the inspection apparatus according to more specific embodiments of the present invention will be described below.

First Embodiment

Figure 1:
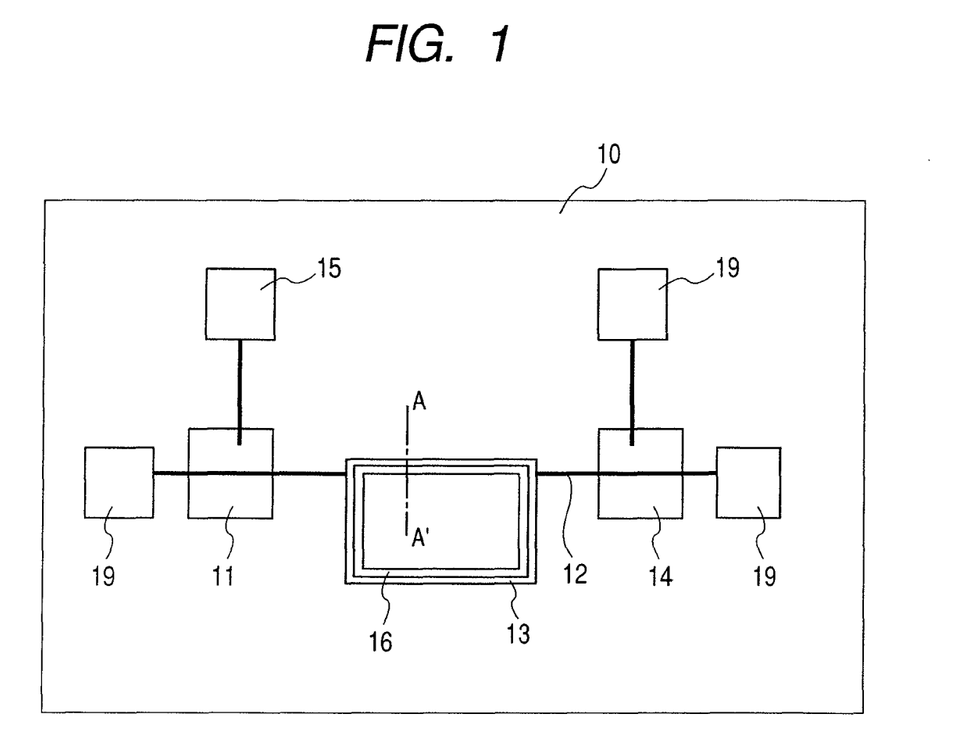
FIG. 1 is a plan view illustrating an inspection apparatus according to a first embodiment of the present invention.

FIG. 1 is a plan view illustrating the configuration of an inspection apparatus according to the present invention. In this embodiment, a photoconductive device 11 using LT-GaAs is used as an electromagnetic wave generating unit. Also, a photoconductive device 14 using LT-GaAs is used as an electromagnetic wave detecting unit as in the electromagnetic wave generating unit. Also, a micro strip line 12 is used as a transmission line. The micro strip line 12 is configured so as to interpose a dielectric material between two metal layers. Because the micro strip line 12 is of the structure in which unnecessary electromagnetic wave propagation modes are suppressed at low frequency waves to terahertz waves, the propagation loss and the dispersion characteristic are relatively excellent. Also, the micro strip line 12 is readily manufactured. In this embodiment, the micro strip line 12 on the substrate 10 is linear, but the photoconductive elements 11 and 14 are integrated together with an interval of about 1 mm in a part of the micro strip line 12. Those two metal layers between which the dielectric material of the micro strip line 12 is interposed are formed of laminated Ti/Au, and the dielectric layer is made of benzocyclobutene (BCB). The BCB is relatively transparent in the region of the terahertz wave, excellent in the chemicals resistance, and easily processable through etching and the like. This embodiment further includes an electrode portion 15 for applying a bias voltage to the photoconductive element 11 of the electromagnetic wave generating unit, and various electrode pads 19.

The structure for helping a part of a detection object 16 mainly of a meniscus configuration which is precipitated from a solution to be selectively deposited along the transmission line 12 is arranged in the vicinity of the transmission line 12. In this embodiment, a liquid holding structure 13 for confining the solution to a given region is used as the structure.

Figure 15:
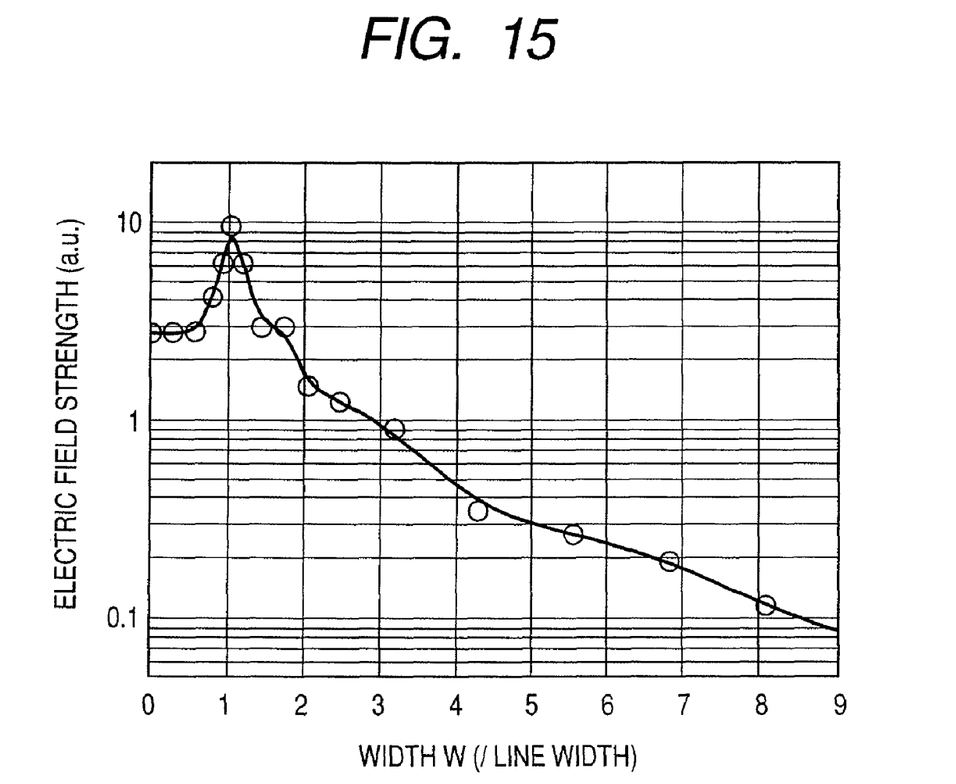
FIG. 15 is a diagram illustrating an electric field distribution of a transmission line.

FIG. 15 is an analysis result regarding the electric field distribution of the micro strip line that can be applied as the transmission line according to this embodiment. FIG. 15 illustrates the electric field strength distribution with respect to a region having a width W normalized by the line width in the micro strip line. For example, in the case of W=1, FIG. 15 illustrates the electric field strength of both edges of the strip line that constitute the micro strip line. Referring to FIG. 15, it is found that a region with an electric field of $1/e^2$ or more of the peak value of the electric field distribution is about 3 W. In other words, a region within a distance of the width of about one line from the edge of the strip line has the detection sensitivity. From this viewpoint, in order to interact the electromagnetic wave that propagates in the micro strip line 12, it is understood that it is desirable to arrange the structure in that region.

Figure 2:
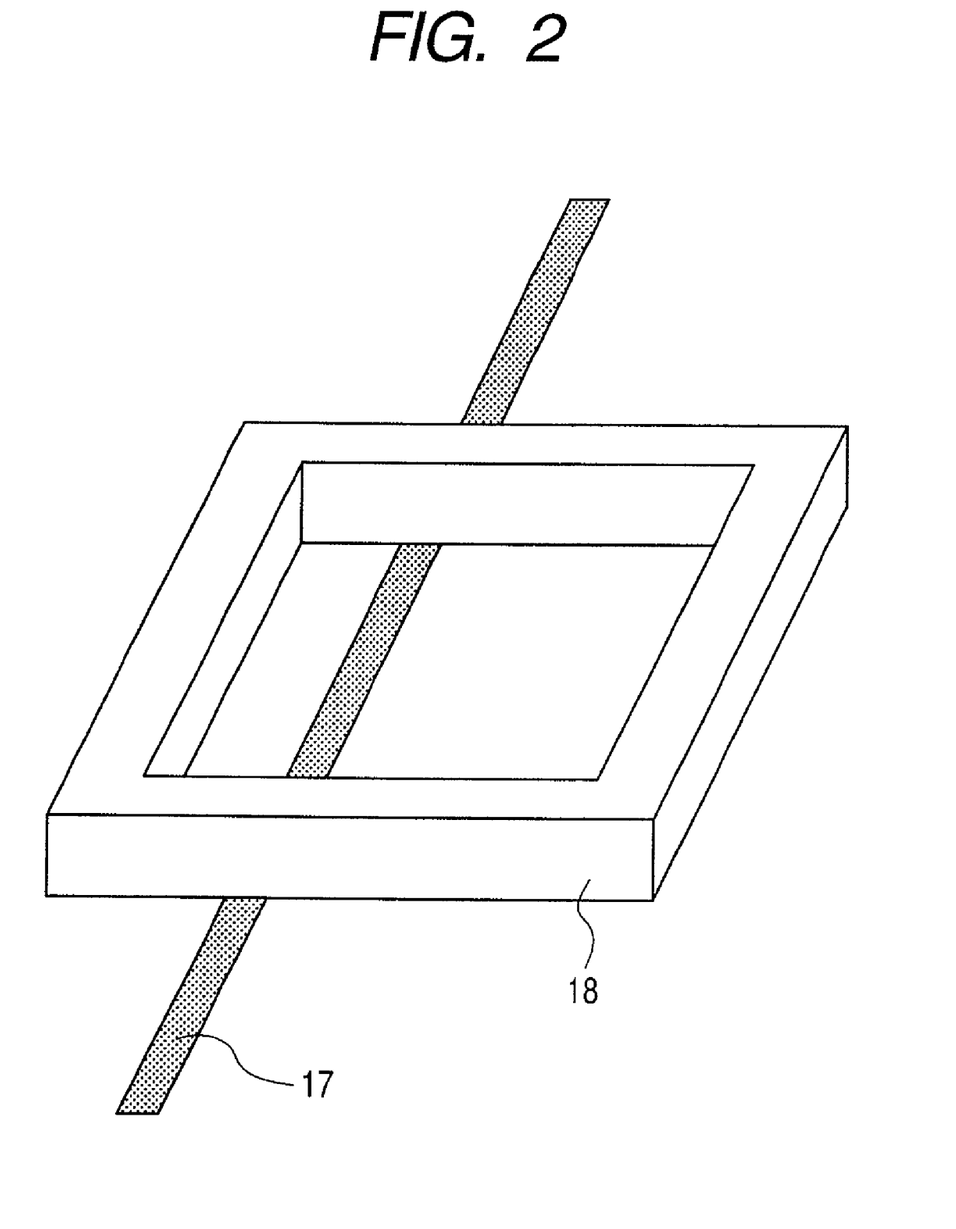
FIG. 2 is a perspective view illustrating an example of a liquid holding structure that is formed in the vicinity of a transmission line.

In this embodiment, the liquid holding structure 13 has a tub structure 18 illustrated in FIG. 2, and it is desirable that a distance between at least one side of the side walls of the liquid holding structure 13 and the micro strip line 12 be equal to or lower than the line width from the edge of the line 17. That is, when it is assumed that the line width of the micro strip line 12 is 10 μm, it is desirable that at least one side of the liquid holding structure 13 be within about 10 μm from the line edge of the micro strip line 12. That is, since the electromagnetic wave of the propagation mode in the micro strip line 12 is held within a distance from the center of the line of three times the line width, it is desirable that the liquid holding structure 13 be formed in view of this. Accordingly, in this embodiment, the distance between the side wall portion of the walled structure (liquid holding structure 13) and the edge of the transmission line (micro strip line 12) is once or less as long as the width of the transmission line. However, the present invention is not limited to the above-mentioned structure. Such a configuration that the side of the liquid holding structure 13 and the micro strip line 12 are apart from each other by the above-mentioned distance or longer is not excluded from the present invention. It is desirable that the material of the liquid holding structure 13 be made of BCB that is used in the micro strip line 12 in view of the above-mentioned features. However, when the material is low in the loss in the region of the terahertz wave, the present invention is not limited to the above-mentioned material.

Subsequently, an example of a manufacturing process according to this embodiment will be described. First, a silicon (Si) substrate with a thermally oxidized film is used, and a metal layer is laminated on the Si substrate. This layer is required when a gold stannum (AuSn) solder layer for bonding on the substrate LT-GaAs used for the photoconductive elements 11 and 14 that will be described later is laminated thereon. In this manufacturing example, Ti/Pd/Au (titanium/palladium/gold) are laminated though a method using sputtering and electric field plating. Then, an AuSn solder layer for transferring the LT-GaAs thin film is laminated to a region where the LT-GaAs thin film is to be produced as the photoconductive elements 11 and 14. The method of laminating the AuSn solder layer is selected from a method of depositing Au and Sn at the same time and a method of alternately laminating Au and Sn by electrolytic plating etc.

A technique of transferring the LT-GaAs thin film used in the generation and detection of terahertz waves will be described below. As an etching stop layer, an aluminium arsenide (AlAs) sacrifice layer is laminated on a high resistivity gallium arsenide (SI-GaAs) substrate. After that, a metal layer is laminated on a LT-GaAs layer that has been grown by and annealed at a low temperature of 250° C., through sputtering or vapor deposition. Then, a bonding device is used to bond a metal surface of the LT-GaAs chip and the metal chip on the Si substrate by means of thermal compression bonding or ultrasonic compression boding. After that, the GaAs substrate and the AlAs sacrifice layer are selectively removed by wet etching, thereby enabling the thin film of LT-GaAs to be transferred. After that, in order to separate LT-GaAs into that for generation and that for detection, photolithography and wet etching are used to remove the unnecessary portion of the LT-GaAs. In this example, GaAs is described as the thin film. However, the present invention is not limited to the above example. As other semiconductors, indium phosphorus (InP) or indium arsenide (InAs) can be used. Also, organic semiconductors having photoconductivity may be used.

Subsequently, a dielectric material is laminated. The dielectric material is made of BCB. The dielectric material is not limited to this material, but may be made of polysilane, polyimide, Teflon (registered trademark), or polyolefin. In order to reduce the dielectric loss in the transmission line, the dielectric material is preferably selected from materials that are small in dielectric tangent from the viewpoint of the high frequency transmission line. The dielectric material is applied on the laminated layer using a spin coater, and thereafter cured by means of an oven or a hot plate.

Then, photolithography and dry etching processes are conducted again to remove a partial region of the BCB so as to expose the LT-GaAs thin film surface. This is because the metal layer of the transmission line is brought into contact with the LT-GaAs surface so that a bias voltage can be vertically or horizontally applied to the LT-GaAs layer using a GND portion and the transmission line portion. Further, this is because the LT-GaAs layer is irradiated with a femtosecond laser so that the terahertz wave can be generated and detected.

A process example will be described below. BCB is laminated on a substrate in a state where an LT-GaAs is transferred onto a metal layer that forms the GND layer. As described above, BCB is applied using a spin coater. Then, a photoresist such as AZ4620 is applied, exposed, and developed, and the BCB layer is patterned. The resist is preferably has a high resistance with respect to a gas used in etching the dielectric material and has an excellent selectivity. The etching of BCB uses $O_2$ and $CF_4$.

After BCB has been etched by the dry etching method, the resist is removed. An example of the removing method includes ashing using oxygen plasma or organic solvent such as acetone by which the resist is melted.

After the LT-GaAs thin film surface has been exposed, the transmission line and the electrode pads are formed. The method therefor is photolithography and liftoff. The transmission line is formed so as to pass on the exposed LT-GaAs thin film. The metal width of the transmission line is about 10 μm, for example, in the case where BCB is laminated in a thickness of about 5 μm, although depending on the dielectric constant and the laminated thickness of the BCB layer.

Finally, the liquid holding structure 13 is fabricated. There are proposed a method of patterning a material by photolithography, and a method of patterning the resist as a mask material through photolithography followed by dry etching the resist.

Figure 5:
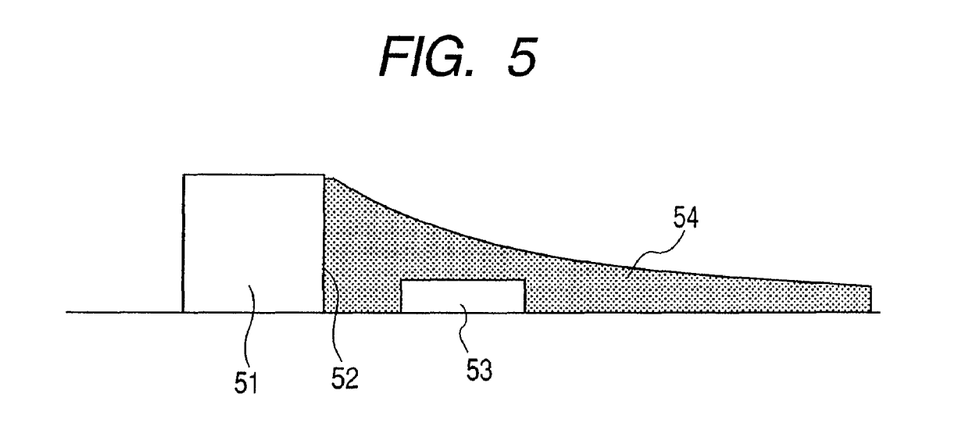
FIG. 5 is a cross-sectional view taken along the line A-A' of FIG. 1 illustrating an appearance when a wettability of a side wall portion of the walled structure according to the first embodiment is large.
Figure 6:
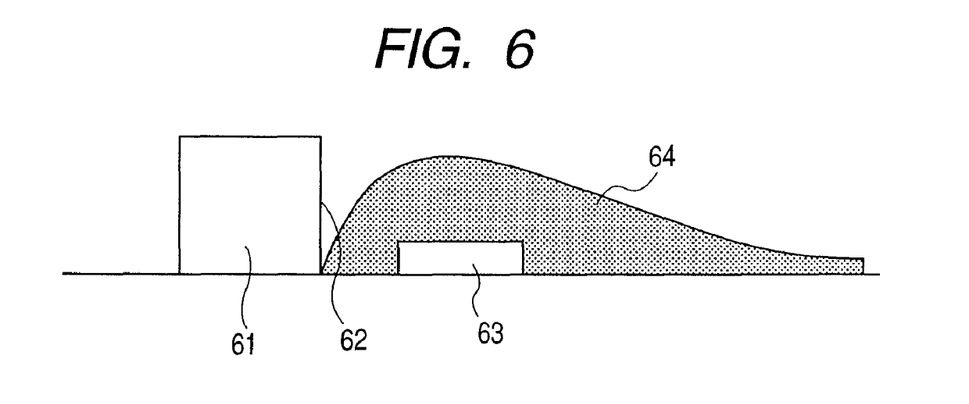
FIG. 6 is a cross-sectional view taken along the line A-A' of FIG. 1 illustrating an appearance when the wetting property of the side wall portion of the walled structure according to the first embodiment is small.

Subsequently, the sensing operation according to this embodiment will be described. First, the deposition of the detection object 16 in the liquid holding structure 13 will be further described in brief. When the buffer solution is dropped within the liquid holding structure 13 by means of the micro injector, the detection object 16 is deposited on a side wall of the base and the liquid holding structure 13 as the buffer solution is evaporated. The behavior of the buffer solution within the liquid holding structure 13 depends on the wetness of the inner wall, the surface tension, the density of the buffer solution, etc. For example, as illustrated in FIG. 5 corresponding to the A'-A sectional view of FIG. 1, when the wetness of the side wall 52 of the liquid holding structure 51 is high, the buffer solution comes into contact with the inner wall 52 due to the capillary phenomenon so as to flatten the buffer solution against the inner wall 52, and is then evaporated while being reserved. As a result, the detection object 54 is deposited on not only the base surface (on which transmission line 53 is formed) of the liquid holding structure 51, but also on the side wall thereof. On the other hand, as illustrated in FIG. 6 corresponding to the A'-A sectional view of FIG. 1, when the wetness of the inner wall 61 is low, the fluid surface is maintained and the solution is evaporated so as to avoid the side wall 62 due to the capillary phenomenon which is caused by the surface tension. As a result, the detection object 64 is hardly deposited on the side wall 62 of the liquid holding structure 61, but is deposited on the base surface (on which transmission line 63 is formed) of the liquid holding structure 61. Accordingly, when the side wall is made of a hydrophobic material, the deposition of the detection object on the side wall can be suppressed. This is a desirable configuration because a meniscus portion can be formed with high controllability and effectively.

As described above, in order to deposit the detection object on a given place, it is necessary to consider the arrangement place and the material of the side wall of the liquid holding structure 13 as well as the material and flatness of the base (surface on which the solution is dropped) of the liquid holding structure 13.

Figure 7:
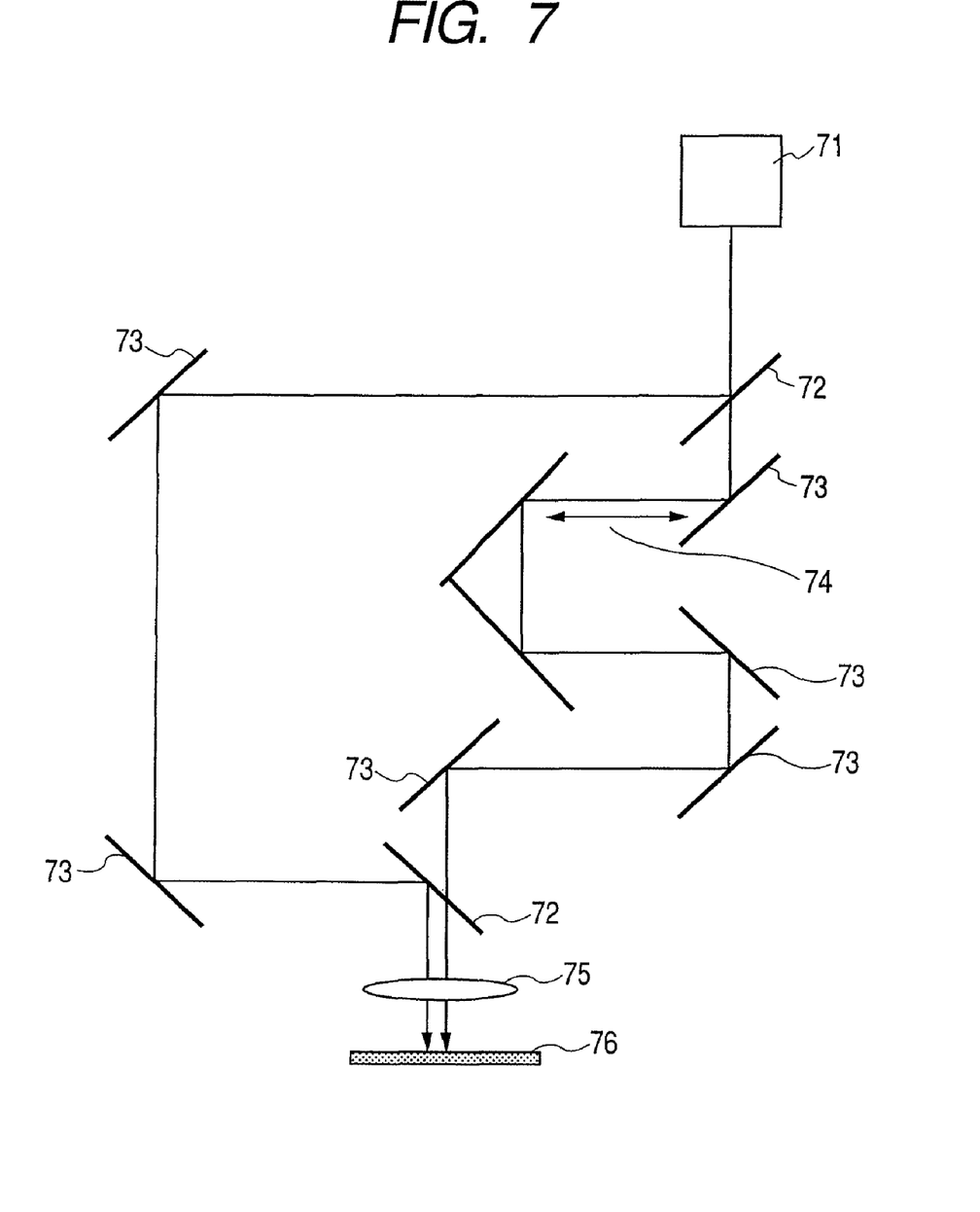
FIG. 7 is a diagram illustrating an entire measurement system when a measurement is conducted according to the first embodiment.

As a measuring method using the device manufactured as described above, there is a measuring method using a THz-TDS (time-domain spectroscopy) method. FIG. 7 illustrates the entire measuring system that can be applied to this measuring method.

A femtosecond pulse laser beam that is output from a femtosecond laser 71 is split into two beams by a beam splitter 72, and the photoconductive element 11 on the generation side within a substrate 76 which is the device of this embodiment is irradiated with one of the split laser beams via an optical path in which a mirror 73 is located. The photoconductive element 14 on the detection side within the substrate 76 is irradiated with the other beam via a delay optical system 74. Both of those optical conductive elements are in close vicinity of each other by an interval of several mm through the transmission line 12, it is desirable to condense the femtosecond pulse laser beam using an objective lens 75. With scanning of the delay optical system 74, the time waveform of the terahertz can be obtained.

Figure 8:
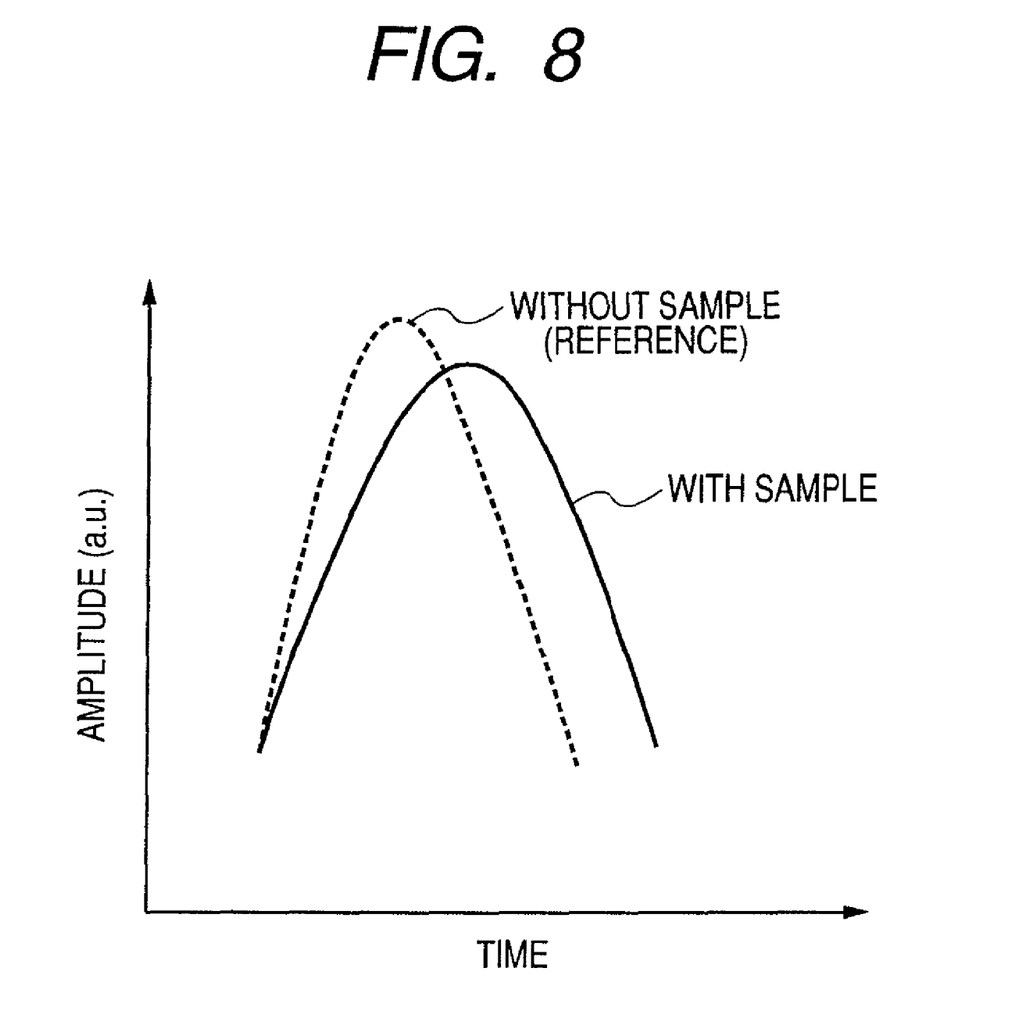
FIG. 8 is a diagram illustrating a difference in a time waveform example of the detected electromagnetic waves between the cases when a detection object is present and when the detection object is absent.

FIG. 8 is an example of the comparison of the time waveform between the cases when the sample (detection object) exists on the transmission line 12 and when the sample does not exist on the transmission line 12 (reference). When the sample exists, electromagnetic waves are affected by the macro complex dielectric constant of the sample to cause time delay or pulse peak attenuation. In this way, information on the detection object is obtained by using electromagnetic wave. The measuring method is not limited to the time-domain spectroscopy. For example, it is possible that the detection intensity of the electromagnetic waves when the detection object does not exist is simply compared with the measurement detection intensity when the detection object exists, thereby inspecting whether the detection object exists, or not.

The configuration described above enables the detection object and electromagnetic waves that propagate through the transmission line to be effectively interacted with each other.

Second Embodiment

Figure 9:
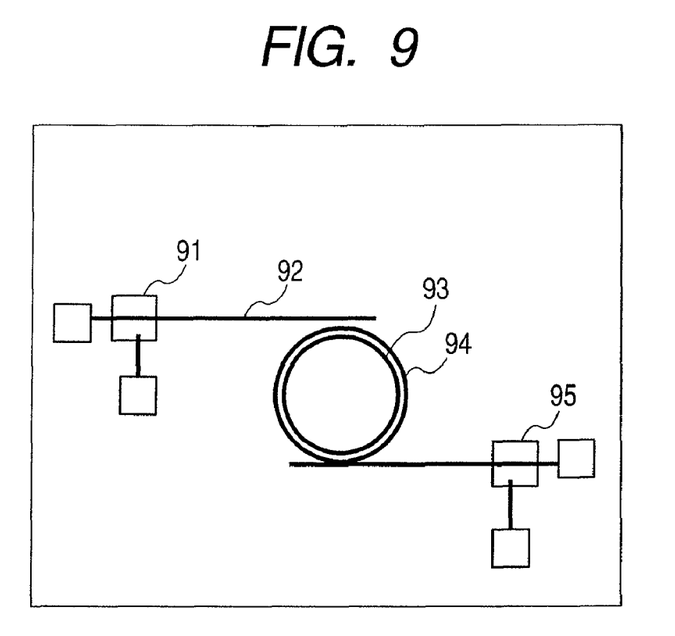
FIG. 9 is a plan view illustrating an inspection apparatus according to a second embodiment of the present invention.

FIG. 9 is a plan view illustrating an inspection apparatus according to a second embodiment of the present invention. In this embodiment, a circular resonator structure 93 is disposed in the middle of a transmission line 92. A liquid holding structure 94 that is the same as that of the first embodiment is disposed around the resonator structure 93. The liquid holding structure 94 that is a deposition assist structure has a circular side wall portion that rises from a surface where the transmission line 92 is formed, in the vicinity of the outside of the resonator structure 93.

As in the first embodiment, the liquid holding structure 94 can be formed through photolithography after a photosensitive BCB is applied on the laminated transmission line 92 by a spinner. The liquid holding structure 94 can be formed even within a method of dry etching a non-sensitive material with the photoresist as a mask. However, in this method, it is necessary to prevent deterioration of the flatness of the base on which the transmission line 92 has been formed.

In this embodiment, when the detection object is dropped inside the liquid holding structure 94, the detection object is deposited along the circular side wall portion inside the liquid holding structure 94. Accordingly, the detection object is deposited on or in the vicinity of the resonator structure 93 which is located just inside the circular side wall portion of the liquid holding structure 94. As a result, the electromagnetic wave that is output from the photoconductive element 91 on the electromagnetic wave generating unit side, propagates along the transmission lines 92 and 93, and is detected by the photoconductive element 95 on the electromagnetic wave detecting unit side changes depending on the existence of the detection object. That is, when the detection object is dropped on the ring-shaped resonator structure 93, the resonant frequency in the ring-shaped resonator structure 93 changes, and the changed resonant frequency is detected by the photoconductive element 95 on the electromagnetic wave detecting unit side. In this way, for example, the macro complex dielectric constant of the detection object is determined, thereby enabling the detection object to be analyzed. With the above-mentioned configuration, it is possible to improve the use efficiency of the detection object.

Third Embodiment

Figure 10:
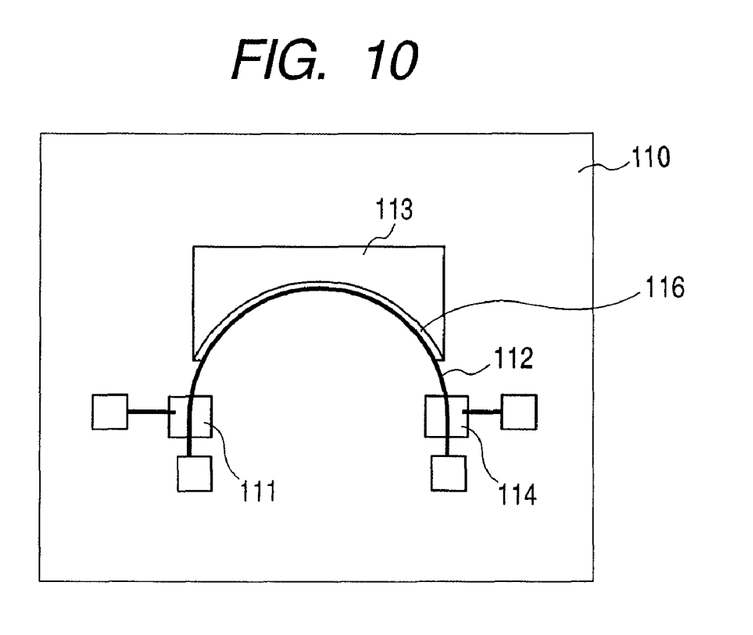
FIG. 10 is a plan view illustrating an inspection apparatus according to a third embodiment of the present invention.

FIG. 10 is a plan view illustrating an inspection apparatus according to a third embodiment of the present invention. The basic structure is the same as that of the first embodiment. Also in this embodiment, a micro strip line 112 is formed on a substrate 110 as a transmission line that extends from a photoconductive element 111 on the electromagnetic wave generating unit side to a photoconductive element 114 on the electromagnetic wave detecting unit side, as in the first embodiment. The micro strip line 112 is configured to have a curvature. It is desirable that the radius of the curvature of the micro strip line 112 be from about several tens to several hundreds of μm, when used as a sensor taking the typical size of spread of the solution including the detection object into consideration. However, a size outside of that range is also acceptable. In this embodiment, for example, there is provided a transmission line having a radius of curvature of about 200 μm.

Outside the micro strip line 112 in the radial direction, is disposed a liquid holding structure 113 having a side wall portion that rises from the surface of the substrate 110. The liquid holding structure 113 is a structure that confines the solution to a given region for helping a meniscus portion 116 which is mainly precipitated from the solution to be selectively deposited on or in the vicinity of the transmission line. In this example, it is desirable that the side wall portion of the liquid holding structure 113 which is a deposition assist structure be located within about 10 μm from the micro strip line 112. In other words, when the radius of curvature of the transmission line 112 is 200 μm, the side wall portion of the liquid holding structure 113 has a radius of curvature of about 220 μm, and is formed toward the inside in the vicinity of the outside of the transmission line 112 in the radial direction. This is because it is desirable that with the propagation mode of the electromagnetic waves in the micro strip line 112, because the electromagnetic wave is held within a distance from the center of the line of about three times the line width, the side wall portion of the liquid holding structure 113 be formed taking this situation into consideration. However, the present invention is not limited to this configuration. Such a configuration that the side wall portion of the liquid holding structure 113 and the micro strip line 112 are apart from each other by the above-mentioned distance or longer is not excluded from the present invention. As described above, in this embodiment, the transmission line has a portion that extends with a curvature, and the side wall portion of the deposition assist structure 113 extends along the portion that extends with a curvature.

In this embodiment, the signal line of the micro strip line 112 is thus formed with a curvature. Accordingly, when a solution containing the detection object 116 therein is dropped inside the radius of curvature of the signal line of the micro strip line 112, the detection object 116 is selectively deposited along the micro strip line 112 in a meniscus configuration. As a result, it is possible to efficiently interact the electromagnetic wave that propagates through micro strip line 112 with the detection object 116. It is desirable that the configuration of the micro strip line 112 be of a circular configuration having a curvature. However, the present invention is not limited to the above-mentioned configuration, and an oval configuration or a liner configuration can be applied. In any cases, it is necessary to dispose the deposition assist structure having the side wall portion that rises from the surface where the transmission line is formed in the vicinity of the transmission line.

With the configuration described above, it is possible to more simply coat a desired portion with the detection object.

Fourth Embodiment

This embodiment further includes a cooling unit for freezing and holding a detection object on or in the vicinity of the transmission line in the applied configurations of the present invention which have been described in the above embodiments. In particular, in a case where the detection object is a volatile material, the amount of the detection object per se may be reduced with evaporation of the solution in the configurations described in the above embodiments. For that reason, in this embodiment, the solution per se is used as a holding unit that holds the detection object by freezing the solution that contains the detection object.

Figure 11:
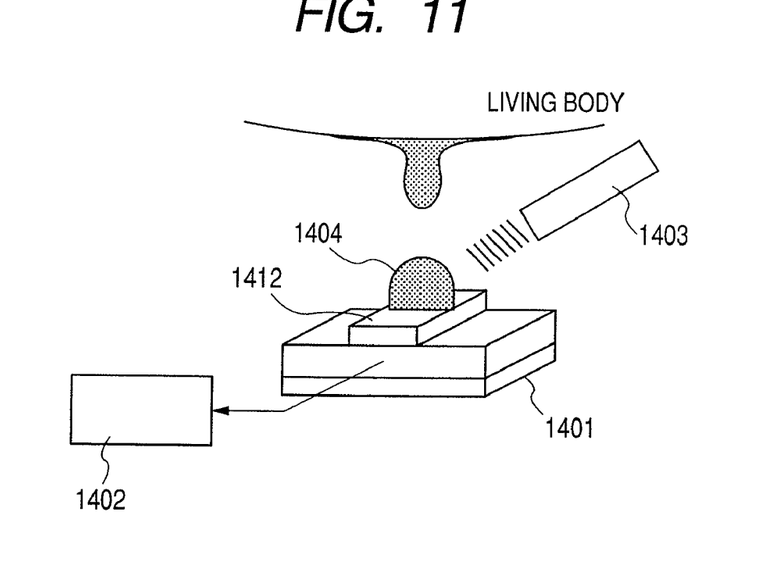
FIG. 11 is a diagram illustrating an inspection apparatus according to a fourth embodiment of the present invention.

FIG. 11 is a schematic structural diagram illustrating an inspection apparatus according to the present invention. As illustrated in FIG. 11, this embodiment includes a transmission line 1401, an electromagnetic wave detecting unit 1402, a cooling unit 1403, and a portion to which a living body sample 1404 is to be dropped. Other structural elements of the electromagnetic wave generating unit and the walled structure which have been described above will be omitted. In this example, the living body sample 1404 is used as the detection object, but the detection object is not limited thereto as long as the detection object can be measured in this embodiment.

For the transmission line 1401, the above-mentioned micro strip line is used. However, the transmission line 1401 is not limited to that structure, and any transmission lines that allow the terahertz waves to be propagated are applicable.

The cooling unit 1403 sprays the living body sample 1404 with a cold spray, and freezes and holds the living body sample 1404 in the vicinity of the transmission line 1401 along the walled structure as a restraint assist structure (not shown). The cooling unit 1403 is not limited to the above-mentioned member as long as the above-mentioned object can be achieved. For example, it is possible that the transmission line 1401 is cooled using a Peltier device that is in close contact with the substrate on which the transmission line 1401 is disposed, thereby indirectly cooling the living body sample 1404. Also, a unit that cools the atmosphere surrounding the transmission line 1401 can be used instead of spraying.

The operation of this embodiment will be described. The living body sample 1404 that has been extracted from the living body is dropped on the transmission line 1401 using a pipetter. In this case, for example, the transmission line 1401 may be brought in direct contact with the living body sample 1404 on the living body without using a dropping unit such as a pipetter. The living body sample 1404 on the transmission line 1401 is developed in the vicinity of a line 1412 (also called "signal line") where electromagnetic waves are strongly distributed in the transmission line 1401 along the structure of the above-mentioned walled structure. In this case, the living body sample 1404 is frozen by the cooling unit 1403, and held on the transmission line 1401. In this state, the propagation state of the terahertz waves that propagate through the transmission line 1401 is detected by the electromagnetic wave detecting unit 1402, to thereby conduct sensing of the detection object.

In this embodiment, the detection object is cooled, thereby reducing thermal fluctuation in the molecule vibration mode, with the result that it is expected to improve the measurement sensitivity. Further, when the solution is frozen, terahertz wave absorption which is attributable to moisture can be also reduced, thereby expecting an improvement in the measurement sensitivity. Also, it is easy to place a liquid detection object at a desired portion by the restraint assist structure.

Fifth Embodiment

Figure 12A:
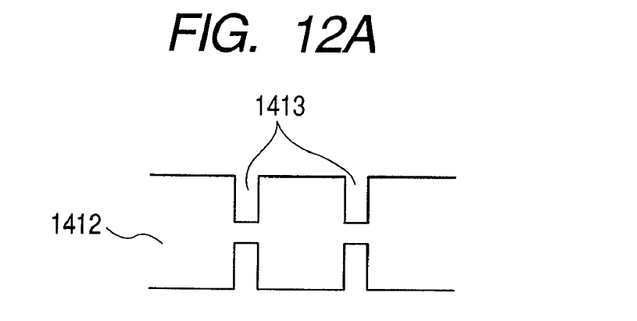
FIGS. 12A and 12B are diagrams illustrating an inspection apparatus according to a fifth embodiment of the present invention.
Figure 12B:
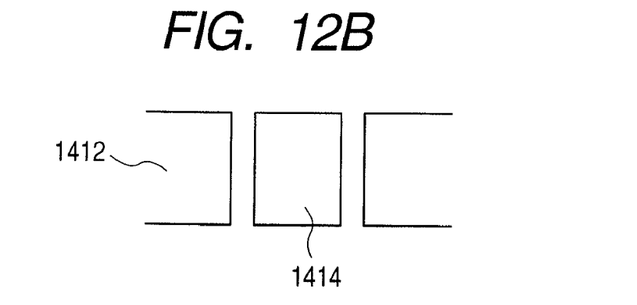

This embodiment further includes a thermal insulation mechanism in the configuration illustrated in the fourth embodiment. More specifically, the thermal insulation mechanism is patterned in a part of the signal line 1412. FIGS. 12A and 12B illustrate structural examples of the thermal insulation mechanism, respectively. The example of FIG. 12A has a recess structure 1413 in a part of the signal line 1412 as the thermal insulation mechanism. The example of FIG. 12B has an isolated conductor 1414 in a part of the signal line 1412.

When a part of the signal line 1412 has the above-mentioned configuration, it is possible to suppress the dispersion of the heat in the signal line and to enhance the cooling effect on a liquid detection object such as a solution that has been dropped on the above-mentioned portion of the signal line. The pattern of the signal line 1412 is not limited to the configuration illustrated in FIGS. 12A and 12B as long as the above-mentioned purpose is attained.

Sixth Embodiment

This embodiment further includes a monitoring unit that monitors the density of the detection object in the configuration illustrated in the fourth embodiment or the fifth embodiment. As the above-mentioned monitoring unit, there is an example illustrated in FIG. 13. In this example, the solution is irradiated with a light 1421 from a light source 1420, and the transmitted light is detected by a detector 1422, to thereby monitor the above-mentioned density from the absorption factor of the solution. The relationship between the absorption factor and the density is measured in advance, and a lookup table containing this relationship is saved in a memory 1424. A processing unit 1423 determines the density on the basis of the detection signal transmitted from the detector 1422 and the lookup table saved in the memory 1424.

Figure 13:
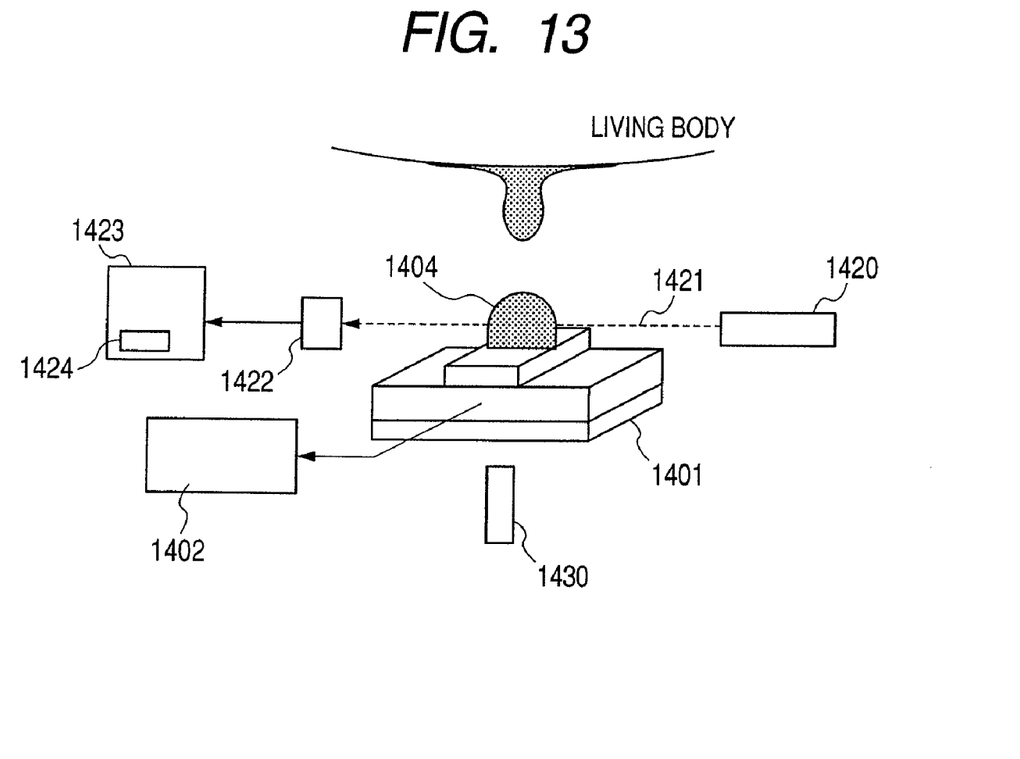
FIG. 13 is a diagram illustrating an inspection apparatus according to sixth and seventh embodiments of the present invention.

With the above-mentioned monitoring unit, for example, the sensing of the detection object is easily conducted under the condition of the same density. As a result, the reliability of the measurement is improved. That is, when monitoring is conducted and the density of the detection object reaches a target density, the detection object is frozen, the electromagnetic wave generating unit is driven, a terahertz wave is propagated through the transmission line 1401, and the propagation state is detected by the electromagnetic wave detecting unit 1402. Thus, the detection object is measured to enhance the reliability of the measurement.

Seventh Embodiment

This embodiment further includes a temperature-dependence monitoring unit that monitors the temperature dependence of the fingerprint spectrum of a detection object, and specifies the constituent material of the detection object in the configuration of the above embodiment. The fingerprint spectrum in the terahertz wave region peculiar to materials is caused by the structure of the detection object or the interaction between molecules. For that reason, when the temperature dependence of the respective spectra is monitored, the quantity or intensity of the frequency shift is found to be different, depending on the constituent material of the detection object. Such information is used as a fingerprint peculiar to materials, thereby expecting an improvement in the precision of specification of the material or structure which constitutes the detection object.

As the unit for monitoring the temperature dependence of the detection object, there are the following examples using a temperature control unit such as a thermometer 1430 illustrated in FIG. 13, a heater or a Peltier device which controls the temperature of the detection object on the signal line. The thermometer 1430 is capable of indirectly measuring the temperature of the detection object when a relationship between the measurement temperature and the temperature of the detection object is grasped in advance. Thus, it is not necessary to measure the temperature of the detection object. In this example, the electromagnetic wave generating unit is driven at measurement temperatures that have been adjusted by the temperature control unit, the terahertz wave is propagated through the transmission line 1401, and the propagation state is detected by the electromagnetic wave detecting unit 1402. Then, the processing section obtains the temperature dependence of the fingerprint spectrum of the detection object on the basis of the signals from the thermometer 1430 and the electromagnetic wave detecting unit 1402. Further, the processing section specifies the constituent material of the detection object with reference to a lookup table of the temperature dependence of the fingerprint spectrum of various materials which have been prepared in advance and saved in the memory.

Eighth Embodiment

This embodiment illustrates an application example that is preferably used in any structure of the above-mentioned inspection apparatus that freeze and hold the detection object, or the combination of those inspection apparatus. More specifically, the inspection apparatus is used as an alcohol detector that detects alcohol density in blood. In this embodiment, for example, sweat on the skin surface of an organism is taken, and the components of sweat are analyzed by this inspection apparatus, to thereby calculate the alcohol density in the blood. In this example, the detection object includes a volatile material. When the detection object is frozen, it is possible to conduct a precise analysis while preventing the volatile material from being evaporated.

Ninth Embodiment

This embodiment illustrates another application example of the eighth embodiment. More specifically, the inspection apparatus is used as a sugar content detector that detects sugar content in blood. In this embodiment, for example, sweat on the skin surface of the organism is taken, and the components of the sweat are analyzed, to thereby calculate the sugar content in the blood. Also in this case, the detection object includes a volatile material. When the detection object is frozen, it is possible to conduct a precise analysis while preventing the volatile material from being evaporated.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-230159 filed Aug. 28, 2006, and Japanese Patent Application No. 2007-063673 filed Mar. 13, 2007, which are hereby incorporated by reference herein in their entirety.

What is claimed is:

1. An inspection apparatus for acquiring information on a measurement object using electromagnetic waves, comprising:
   a substrate;
   a transmission line that is formed on the substrate;
   an electromagnetic wave generating unit for supplying an electromagnetic wave to the transmission line;
   an electromagnetic wave detecting unit for detecting the electromagnetic wave that has propagated through the transmission line; and
   a walled structure,
   wherein the walled structure includes a side wall portion that extends along the transmission line within a region in which the electromagnetic wave that propagates through the transmission line and the measurement object interact with each other, and
   wherein a distance between the side wall portion of the walled structure and an edge of the transmission line is once or less the width of the transmission line.

2. An inspection apparatus according to claim 1, wherein the walled structure comprises a deposition assist structure that helps at least a part of a detection object that is precipitated from the measurement object that is dropped on the substrate to be deposited within the region in which the electromagnetic wave that propagates through the transmission line and the measurement object interact with each other.

3. An inspection apparatus according to claim 1, wherein the walled structure comprises a restraint assist structure that helps at least a part of the detection object that is dropped on the substrate to be restrained within the region in which the electromagnetic wave that propagates through the transmission line and the measurement object interact with each other.

4. An inspection apparatus according to claim 3, further comprising a cooling unit for cooling the measurement object including the detection object which is dropped on the substrate to freeze and hold the measurement object on or in the vicinity of the transmission line.

5. An inspection apparatus according to claim 4, further comprising a heat insulation mechanism that is disposed in a portion of the transmission line.

6. An inspection apparatus according to claim 3, further comprising a monitoring unit for monitoring a density of the measurement object including the detection object that is dropped on the substrate.

7. An inspection apparatus according to claim 1, wherein the transmission line has a portion that extends with a curvature, and wherein the side wall portion of the walled structure extends along the portion that extends with the curvature.

8. An inspection apparatus according to claim 1, wherein the side wall portion of the walled structure is made of a hydrophobic material.

9. An inspection apparatus according to claim 1, wherein the transmission line is a micro strip line.

10. An inspection apparatus according to claim 1, further comprising a temperature-dependence monitoring unit for monitoring temperature dependence of the detection object in the measurement object that is dropped on the substrate.

11. An inspection apparatus according to claim 1, wherein a frequency of the electromagnetic wave includes a frequency band of at least a part of 30 GHz to 30 THz.

12. An inspection method for acquiring information on a measurement object using the inspection apparatus according to claim 1, comprising detecting results of interaction between the detection object within the measurement object and the electromagnetic wave that propagates through the transmission line to inspect the detection object.

13. An inspection method for acquiring information on a measurement object using the inspection apparatus according to claim 10, comprising detecting temperature dependence of the interaction between the detection object within the measurement object and the electromagnetic wave that propagates through the transmission line to inspect the detection object.

* * * * *